US012688933B2

(12) United States Patent
Murthy et al.

(10) Patent No.: US 12,688,933 B2
(45) Date of Patent: Jul. 21, 2026

(54) LIVING BODY INFORMATION ACQUISITION SYSTEM, HEALTH MANAGEMENT SERVER, AND SYSTEM

(71) Applicant: ATONARP INC., Tokyo (JP)

(72) Inventors: Prakash Sreedhar Murthy, Tokyo (JP); Kazuo Okemoto, Tokyo (JP); Akira Imai, Tokyo (JP)

(73) Assignee: ATONARP INC., Tokyo (JP)

( * ) Notice: Subject to any disclaimer, the term of this patent is extended or adjusted under 35 U.S.C. 154(b) by 642 days.

(21) Appl. No.: 17/281,341

(22) PCT Filed: Oct. 4, 2019

(86) PCT No.: PCT/JP2019/039313
§ 371 (c)(1),
(2) Date: Mar. 30, 2021

(87) PCT Pub. No.: WO2020/071542
PCT Pub. Date: Apr. 9, 2020

(65) Prior Publication Data
US 2022/0044801 A1 Feb. 10, 2022

(30) Foreign Application Priority Data

Oct. 4, 2018 (JP) .................................. 2018-189523

(51) Int. Cl.
*G16H 40/67* (2018.01)
*G01N 21/65* (2006.01)
(Continued)

(52) U.S. Cl.
CPC ............. *G16H 40/67* (2018.01); *G01N 21/65* (2013.01); *G01N 33/493* (2013.01); *G01N 33/94* (2013.01); *G06K 7/1417* (2013.01)

(58) Field of Classification Search
CPC ........ G16H 10/00; G16H 10/20; G16H 10/40; G16H 15/00; G16H 20/00; G16H 20/10;
(Continued)

(56) References Cited

U.S. PATENT DOCUMENTS

| | | | | | |
|---|---|---|---|---|---|
| 5,073,500 | A | * | 12/1991 | Saito | ........................ A61B 5/20 |
| | | | | | 4/300 |
| 5,815,260 | A | * | 9/1998 | Dou | ...................... A61B 10/007 |
| | | | | | 356/301 |

(Continued)

FOREIGN PATENT DOCUMENTS

| | | |
|---|---|---|
| EP | 0483566 B1 | 8/1995 |
| JP | H01207662 A | 8/1989 |

(Continued)

OTHER PUBLICATIONS

Kawarada et al. 1998, "Evaluation of automated health monitoring system at the "Welfare Techno House"," Proceedings of the 20th Annual International Conference of the IEEE Engineering in Medicine and Biology Society. vol. 20 Biomedical Engineering Towards the Year 2000 and Beyond (Cat. No. 98CH36286), Hong Kong, Chi.*

(Continued)

*Primary Examiner* — Robert W Morgan
*Assistant Examiner* — Charles P Coleman
(74) *Attorney, Agent, or Firm* — BUCHANAN INGERSOLL & ROONEY PC

(57) ABSTRACT

A health management system includes a plurality of living body information acquisition systems and a health management server. Each living body information acquisition system includes a data acquisition module that acquires body monitoring data including information on urine components contained in a urine sample collected from urine excreted into a toilet bowl; and a toilet bowl identification module (Continued)

configured so that a user terminal acquires toilet bowl identification information for identifying a toilet bowl in use by the user in a contactless manner. Each living body information acquisition system outputs individual health monitoring information including the body monitoring data associated with user identification information that identifies the user when using the toilet bowl by way of the toilet bowl identification information in units of urination.

14 Claims, 4 Drawing Sheets

(51) Int. Cl.
|  |  |
|---|---|
| *G01N 33/493* | (2006.01) |
| *G01N 33/94* | (2006.01) |
| *G06K 7/14* | (2006.01) |

(58) Field of Classification Search
CPC ........ G16H 20/13; G16H 20/17; G16H 30/00; G16H 40/00; G16H 50/00; G16H 70/00; G16H 40/67; G06Q 50/22–24; G01N 21/65; G01N 33/493; G01N 33/94; G06K 7/1417
USPC .................................................. 705/2, 3, 20
See application file for complete search history.

(56) References Cited

U.S. PATENT DOCUMENTS

| | | | | |
|---|---|---|---|---|
| 2009/0099781 | A1 | 4/2009 | Miyashita | |
| 2010/0008859 | A1 | 1/2010 | Scharschmidt | |
| 2015/0334108 | A1* | 11/2015 | Khalil ................. | H04L 63/0815 |
| | | | | 726/8 |
| 2017/0322197 | A1* | 11/2017 | Hall ..................... | G01N 33/493 |
| 2018/0149666 | A1* | 5/2018 | Hall ........................ | G01N 33/94 |
| 2018/0163387 | A1* | 6/2018 | Staton ................... | A61B 5/207 |
| 2018/0371735 | A1* | 12/2018 | Hall ..................... | A61B 5/1455 |
| 2021/0074402 | A1* | 3/2021 | Levin ..................... | G16H 20/10 |
| 2022/0044801 | A1* | 2/2022 | Murthy ................. | G16H 50/20 |
| 2022/0211354 | A1* | 7/2022 | Kashyap ............ | A61B 10/0038 |

FOREIGN PATENT DOCUMENTS

| | | | |
|---|---|---|---|
| JP | H04164214 | A | 6/1992 |
| JP | H0545356 | A | 2/1993 |
| JP | H09171015 | A | 6/1997 |
| JP | 2000126138 | A | 5/2000 |
| JP | 2004166985 | A | 6/2004 |
| JP | 2005106621 | A | 4/2005 |
| JP | 2012501451 | A | 1/2012 |
| JP | 2013092537 | A | 5/2013 |
| JP | 2013156919 | A | 8/2013 |
| JP | 2016057979 | A | 4/2016 |
| JP | 2016097108 | A | 5/2016 |
| JP | 2017054373 | A | 3/2017 |
| JP | 6569027 | B1 | 8/2019 |
| WO | 2004114180 | A1 | 12/2004 |
| WO | 2010134543 | A1 | 11/2010 |

OTHER PUBLICATIONS

Bae et al. 2018,"User Health Information Analysis With a Urine and Feces Separable Smart Toilet System," in IEEE Access, vol. 6, pp. 78751-78765, 2018, doi: 10.1109/ACCESS.2018.2885234.*

Notification of Transmittal of Translation of the International Preliminary Report on Patentability issued in corresponding PCT International Application No. PCT/JP2019/039313, dated Apr. 15, 2021 (10 pages).

Asada, Megumi, non-official translation "Easy to check with just a smartphone! Symax's physical condition analysis with QR code authentication", Symax, Inc., <URL:https://media.symax.jp/1408/>, Sep. 13, 2019, 5 pages.

International Search Report (PCT/ISA/210) and Written Opinion (PCT/ISA/237) mailed on Jan. 7, 2020, by the PCT/JP2019/039313 Patent Office as the International Searching Authority for International Application No. PCT/JP2019/039313.

Iwasaki, "Development of a Drinking Management System for Infants, a severity fourth", National Conference Collection (4) interface computer, a human society, Japan, a General Incorporated Information Processing Society, 2012, 03, (5 pages).

Office Action (Notice of Reasons for Refusal) issued on Sep. 28, 2023, by the Japanese Patent Office in corresponding Japanese Patent Application No. 2020-187746, and an English Translation of the Office Action. (8 pages).

* cited by examiner

LIVING BODY INFORMATION ACQUISITION SYSTEM, HEALTH MANAGEMENT SERVER, AND SYSTEM

TECHNICAL FIELD

The present invention relates to a living body information acquisition system, a health management server, and a system that include measurement of urine components.

BACKGROUND ART

Japanese Laid-open Patent Publication No. 2004-166985 describes a health management system that enables users to automatically receive a medical checkup which is similar to that provided by a doctor simply by going about their daily life. In this system, a toilet bowl in a private home, a hospital terminal, a dietitian's terminal, and a home terminal are connected via the Internet. The toilet in the home has a function of automatically determining one of negative, positive, and neutral for a urinary analyte every time the toilet is used, a function of transmitting analysis result data for the urine components to the hospital terminal, and a display function. The hospital terminal has a function of automatically analyzing the health status of an elderly person every time analysis result data is received from a toilet in the elderly person's home and a function of transmitting, when an abnormality has been recognized by the analysis, symptoms of that abnormality to the elderly person's toilet so that the symptoms can be displayed. On receiving the symptoms from the hospital terminal, the dietitian's terminal automatically selects a most suitable meal menu from a sample menu list stored in a menu database and presents the selected meal menu to the toilet in the home and the home terminal. On receiving symptoms from the hospital terminal and a meal menu from the dietitian terminal, the home terminal displays the received information.

Japanese Laid-open Patent Publication No. 2005-106621 discloses a toilet unit with a hygienic and well-designed urine-collecting mechanism that causes no loss in usability as a toilet bowl and enables highly accurate qualitative and quantitative measurement of specific components contained in urine. The toilet unit includes: a pool and trap as a means for capturing the user's urine separately to the sewage; a bowl surface for holding the pool; a level varying means for changing the water level of the pool, and a urine collecting means for collecting the user's urine. The urine collecting means is constructed on the bowl surface and the level varying means of the pool is controlled so that the urine collecting means is positioned below the water level of the pool when a urine collecting operation is not being performed and is positioned above the water level of the pool during a urine collecting operation.

SUMMARY OF INVENTION

Although the cited references describe the idea of analyzing health status by measuring components of urine excreted into a toilet bowl, in reality, systems that measure components in urine excreted into a toilet bowl have not entered general usage. One reason for this is that the components in urine are affected by meals, water intake, perspiration, and the like, and greatly fluctuate over time even within a single day. In addition, although urine does contain many components that indicate the health status, it is necessary to feed back the result of measuring urine components to the user in a simple and secure manner.

One aspect of the present invention is a living body information acquisition system including: a data acquisition module configured to acquire body monitoring data (biological monitoring data) including information on urine components (constituents) contained in a urine samples collected continuously or intermittently from at least part of urine excreted into a toilet bowl; a first identification module configured so that a terminal of a user acquires toilet bowl identification information, which identifies the toilet bowl in use by the user, in a contactless manner (without contact); and an output module configured to output health monitoring information of an individual including the body monitoring data that is associated with user identification information that identifies the user when using the toilet bowl by way of the toilet bowl identification information in units of urination (urination units). One example of the first identification module is a two-dimensional code such as a QR code (registered trademark). It is possible to gather (acquire) health monitoring information for each user without creating a situation where the inside of a toilet where a toilet bowl is installed is monitored from outside using images, sound, or the like.

The system may further include a second identification module configured to acquire body identification information (biometric information) associated with the user identification information that identifies the user when using the toilet bowl, and the output module may include a module configured to output the health monitoring information of the individual (personal or private health monitoring information) associated with the body identification information or the user identification information.

In their day-to-day lives, many people urinate not in a single toilet but in toilets provided in many places, such as homes, offices, public toilets in train stations and expressway service areas, and toilets provided on means of transport such as trains and planes. Body monitoring data acquired by living body information acquisition systems attached to respective toilet bowls is associated with the toilet bowl identification information acquired by a user terminal, for example, a mobile phone, a smartphone, smart glasses, a smart watch, or another wearable terminal, and by accumulating the information in a health management server via a network (the cloud or a computer network) for example, it becomes possible to gather urine information from various locations, which can be useful for health management. As one example, it is possible to estimate excreted amounts in collected urine (accumulated urine) for one day and to estimate the health status based on this. In addition, it is also possible to estimate the user's health status at certain times from fluctuations in concentration of urine components, intervals between urination, and the like, which makes it possible to prevent various symptoms such as heat stroke and health conditions caused by overwork. An application (or program or program product) that enables the functions of a health management server to be realized on a personal terminal may be provided by being recorded on a recording medium.

The data acquisition module may include: a sampling module configured to continuously or intermittently collect at least part of excreted urine and discharge the urine through a translucent detecting section; and an analysis module configured to irradiate the detecting section (detecting part) with light to acquire information on the urine components contained in the urine samples. A typical sampling module may be a module configured to continuously or intermittently collect at least part of the urine excreted into the toilet bowl and discharge the urine through a translucent detecting section into the toilet bowl. A typical analysis module may include a module configured to irradiate the urine samples with lasers to obtain Raman spectra.

By combining a flow-type sampling module that continuously or intermittently collects at least part of the urine excreted into a toilet bowl and discharges the urine through a translucent detecting section into the toilet bowl, and an analysis module that can indirectly measure the components contained in a fluid in real time using lights, such as an analyzer apparatus that uses a Raman spectra (Raman scattering light), it is possible to acquire all of the urine components contained in a urine sample from the beginning to the end of one urination in a urination unit together with the elapsed time. Accordingly, with this living body information acquisition system, it is possible to acquire information on urine components at desired timing, for example, urine components at an intermediate time during urination, to acquire information on the urine components at the start of urination or the end of urination, and to also acquire information in a unit of urination, that is, urine components from the start until the end of urination. This means that information on the urine components for estimating the health status can be obtained at suitable timing for estimating the health status (health states, health conditions).

In addition, for toilet bowls with a flushing function, it is possible to distinguish the flushing liquid from the components of the sampled urine. This means that it is possible to accurately measure the amount excreted in one urination using time or an appropriate mechanism for measuring flow rate, so that the total amount of excreted urine components can be estimated based on information on the measured urine components. It is also possible to estimate based on components in collected urine (stored or accumulated urine).

Another aspect of the present invention is a health management server that is provided with health monitoring information via a network from a plurality of living body information acquisition systems. This health management server may include a health monitoring module configured to analyze the body monitoring data of a user identified by way of toilet bowl identification information acquired via a user terminal or by user identification information established by a body information acquisition system and provide information relating to a health status of the user via a network to a display of a body information acquisition system corresponding to a toilet bowl in use by the identified user or to a terminal of the identified user.

Yet another aspect of the present invention is a health management system including a health management server and a plurality of living body information acquisition systems that are capable of communicating with the health management server via a network (or computer network or the cloud).

Yet another aspect of the present invention is a method of supporting health of individuals via information acquisition systems. Each of information acquisition systems includes a data acquisition module configured to detect urine components contained in urine samples collected continuously or intermittently from at least part of urine excreted into a toilet bowl; a first identification module configured so that a terminal of the user acquires toilet bowl identification information, which identifies the toilet bowl in use by the user, in a contactless manner; and an output module. The method includes the following steps:

the data acquisition module acquiring body monitoring data including information on the urine components;

establishing user identification information on the user when using the toilet bowl by way of the toilet bowl identification information obtained from the terminal before, after, or in parallel with acquisition of the body monitoring data; and the output module outputting personal health monitoring information including the body monitoring data which has been associated with the user identification information in urination units.

Yet another aspect of the present invention is a program (program product) including instructions that cause a computer to function as a health management server as described above. The program can be provided by being stored on a recording medium of an appropriate form. Other aspects, objects, and effects of the present invention will be described in more detail below.

DESCRIPTION OF EMBODIMENTS

Figure 1:
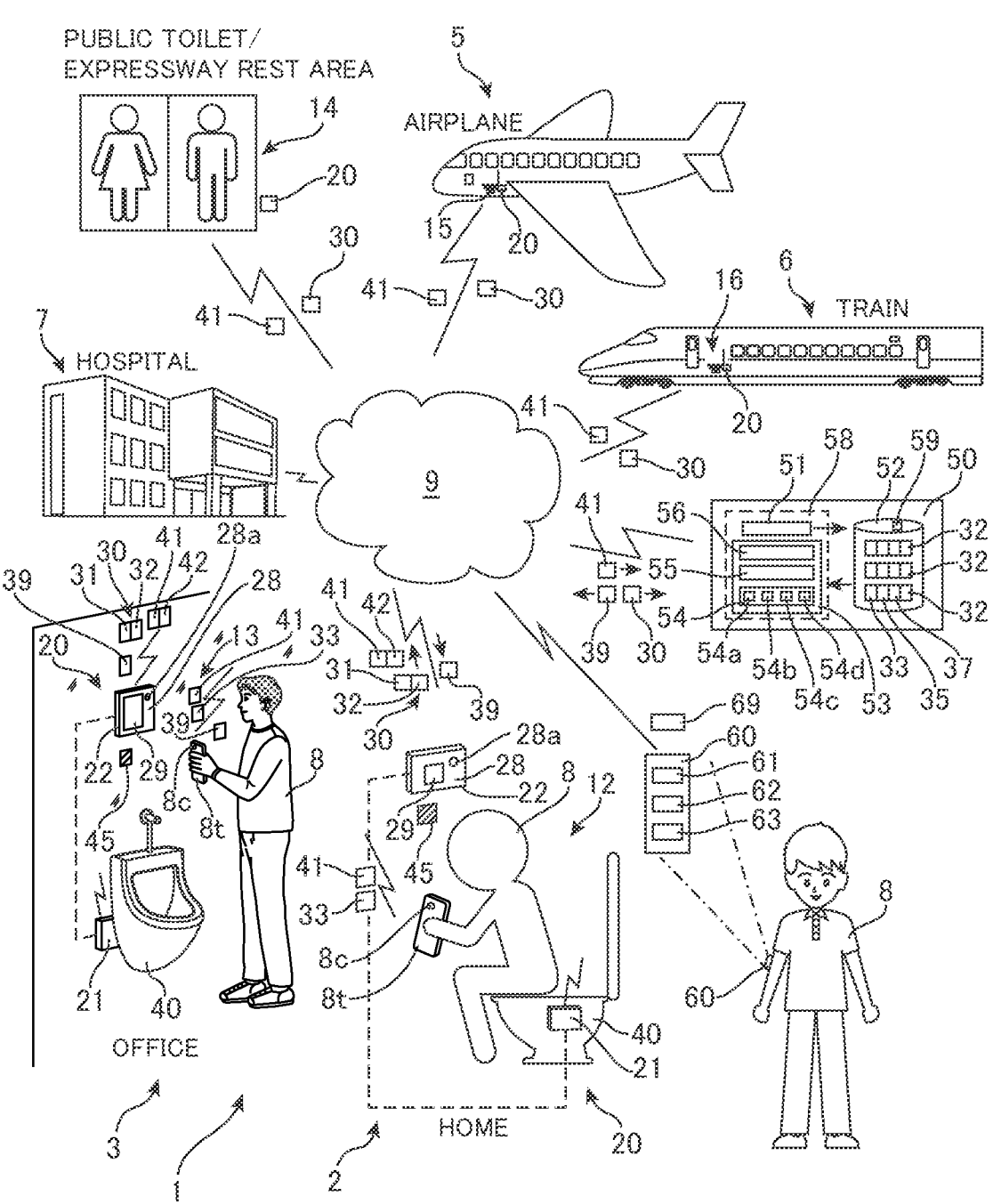
FIG. 1 is a block diagram depicting one example of a health management system.

FIG. 1 depicts an overview of a health management system capable of gathering information from toilets in various locations. This health management system 1 includes: living body information acquisition systems (biological information acquisition systems) 20 that are respectively installed in toilets including a toilet 12 of a home 2 of the user 8, a toilet 13 at an office 3 where the user 8 works, a public toilet 14 at a station, expressway rest area, or the like, a toilet 15 in an airplane 5, a toilet 16 on a train 6 like the bullet train, and the like, and a health management server 50 that is supplied with health monitoring information (health monitoring data) 30 via the cloud (network, computer network, or the Internet) 9 from the respective living body information acquisition systems 20.

The health monitoring information 30 provided by each living body information acquisition system 20 includes body monitoring data (biological monitoring data) 32 including information on components (urine components, urine constituents) contained in urine excreted by the user 8 into the respective toilets 12 to 16. The health monitoring information 30 may include identification information (toilet bowl identification information) 41 of the toilet bowl 40 from which the body monitoring data 32 was acquired, and attribute data (property data, environment data) 42 including information on the acquisition environment of the body monitoring data 32 such as the date relating to time (time stamp) and temperature when the body monitoring data 32 was acquired.

The health monitoring information 30 may include body identification information (biometric identification information, biometric information) 31 for identifying the user 8. Examples of the body identification information 31 may include facial recognition information, retina recognition information, and fingerprint recognition information. The body identification information 31 can be obtained in a contactless manner by processing images obtained from a camera 28a of each living body information acquisition system 20. Facial recognition information or retina authentication information that can be acquired without any special operation is also suitable as the body identification information 31. The body identification information 31 is not limited to information, such as facial recognition information, which relates to the body (human biometric), and may be information, an ID, authentication data, or the like that specifies the user 8 as an individual who has been identified or authenticated by the facial recognition information.

The body monitoring data 32 may include information on components contained in a single excretion of urine (which is the "urination unit" or "unit of urination") into the toilet bowls 40 of the respective toilets 12 to 16 together with the elapsed time and the flow rate (excreted amount of urine). The body monitoring data 32 may further include information such as the body temperature and complexion that is indirectly obtained by using infrared rays or the like. The body monitoring data 32 is data on the human body (body) that can be acquired inside the toilets 12 to 16, and may be information that can be obtained from the body while avoiding contact with the body itself to the greatest degree possible.

The health management server 50 includes: a body monitoring data collecting module (gathering module, collector) 51 that collects and accumulates body monitoring data 32 obtained from the plurality of living body information acquisition systems 20 disposed in the toilets 12 to 16 at different locations in a database 52 in units of user identification information 33 that identifies different users 8; and a health monitoring module (health monitor) 53 that is configured to analyze the body monitoring data 32 of a user 8 accumulated in the database 52 and to provide (feed back) information (health information) indicating a health status to the user 8. When the health monitoring information 30 contains body identification information 31 of a user 8, the body monitoring data collecting module 51 identifies the user 8 using the body identification information 31 and associates the user identification information 33 and the body monitoring data 32 with each other. If the health monitoring information 30 does not include the body identification information 31, the toilet bowl identification information 41 transmitted from the terminal 8*t* of the user 8 and the toilet identification information 41 included in the health monitoring information 30 are referenced along with time stamps and the like included in the respective information, to associate the user identification information 33 and the body monitoring data 32 with each other.

The living body information acquisition systems 20 provided in units of the toilet bowls 40 each include a first identification module (toilet bowl identification module, toilet bowl identifier) 45 that is configured so that the terminal 8*t* of the user 8 can acquire toilet bowl identification information 41 for identifying or recognizing the toilet bowl 40 in use by the user 8 in a contactless manner (without contact). One example of the toilet bowl identification module 45 is a two-dimensional code such as a QR code (registered trademark) provided at (attached to) an easy-to-see (easy-to-find) location, such as the toilet wall or the back of the toilet door. When the user 8 takes a photograph of a toilet bowl identification module (toilet bowl identifier) 45 using a camera 8*c* of the terminal 8*t*, the toilet bowl identification information 41 is acquired contactlessly and the toilet bowl identification information 41 is transmitted to the health management server 50. The terminal 8*t* may supply the user identification information 33 together with the toilet bowl identification information 41 to the health management server 50, and may supply information including the date and time (time stamp) when the toilet bowl identification information 41 was acquired to the health management server 50. The user identification information 33, the time stamp, and the like may be automatically generated in the body monitoring data collecting module 51 at the time when the body monitoring data collecting module 51 received the toilet bowl identification information 41 from the terminal 8*t*, based on the date and time of receiving the toilet bowl identification information 41, registration information of the terminal 8*t* of the user 8, and the like.

The toilet bowl identification module 45 may provide the toilet bowl identification information 41 through communication with the terminal 8*t* using short-range wireless communication (NFC (Near Field Communication)). The toilet bowl identification module 45, which enables the toilet bowl identification information 41 to be acquired by the camera 8*c* of the terminal 8*t* by way of a two-dimensional code or the like, is capable of providing information relating to user identification, including information on the terminal 8*t*, to the health management server 50 using a different communication route to the body information acquisition system 20. This makes it possible to increase security for information relating to the user 8. In addition, a toilet bowl identification module 45 of this type where identification information such as a code is photographed by the terminal 8*t* has many merits including a low initial cost and maintenance cost, and a simple configuration that does not depend on the communication standard used for communicating with the terminal 8*t*. In addition, by providing the toilet bowl identification module 45, it becomes unnecessary to monitor the inside of the toilet where the toilet bowl 40 is installed with a camera or the like for the purpose of acquiring the body identification information 31, which is advantageous in terms of protecting privacy. The terminal 8*t* that acquires the toilet bowl identification information 41 is not limited to a mobile phone, such as a smartphone, and may be another wearable communication terminal, such as a smart watch or smart glasses.

The health monitoring module 53 of the health management server 50 may feed back information (health information) 39 relating to the health status so that the health information is displayed in real time on the display 29 of the living body information acquisition system 20 in the toilet where the user 8 is urinating, or may feed back the health information 39 so that the health information 39 is displayed on the mobile terminal 8*t* that has been registered by the user 8. In addition to information on the internal state of the body, such as whether the concentrations of various marker substances included in the urine components are within ranges judged to be normal, the health information 39 may include advice on how to deal with heat stroke, including whether the amount of water intake is sufficient based on the amount and frequency of urination and/or advice on food and alcohol consumption determined from the urine components.

The health monitoring module 53 may include a urine component analysis module (urine component analyzer) 54 which is configured to analyze data relating to urine components included in the body monitoring data 32, a health diagnosis module (health diagnosis part) 55 configured to judge the health status of the user 8 by referring to the analysis result of the urine component analysis module 54, and a drug monitoring module (drug monitor) 56 configured to estimate excreted amounts of drugs. In addition to the analysis result of the urine component analysis module 54, the diagnosis module 55 may refer to other body information, such as body temperature, included in the body monitoring data 32 for determining the health status (health conditions) of the user 8, and a diagnosis result 35 from a hospital 7 that the user 8 is attending or where the user 8 has undergone a health examination may be referred to as well.

The drug monitoring module 56 may refer to a prescription 37 of medical drugs that have been prescribed by the hospital 7 and perform monitoring of drug treatment, including the effect of medication. The drug monitoring module 56 may perform pharmacokinetic/pharmacodynamic (PK/PD) modelling of individuals, or may monitor tailor-made drug therapies that are suitable for the symptoms and drug metabolism of individuals.

The urine component analysis module 54 typically includes a module 54a configured to refer to information on urine components for a specific time in a urination unit (specific time of each unit of urination) included in the body monitoring data (biological monitoring data) 32 and to generate information relating to health conditions, for example, the information 39 indicating the health status, a module 54b configured to refer to information on urine components for the total elapsed time of a urination unit (each unit of urination) and generate information 39 relating to health status, a module 54c configured to refer to information in which urine components for a plurality of units of urination have been accumulated and generate information 39 relating to health status, and a module 54d configured to refer to fluctuations in the urine components in a plurality of units of urination and generate information 39 relating to health status.

One example of the health management server 50 is a server (computer) equipped with computer resources such as a CPU and memory. It is possible to implement the functions described above in a computer by having a program 59 stored in a memory 52 executed by a CPU 58. It is also possible to provide functions as a personal health management server 50 as application software (or simply "an application"). Functions as the health management server 50 may be implemented on the personal terminal 8t.

The health management system 1 may include other types of living body (biological) monitoring devices that are connected to the network (cloud) 9. One example of a body monitoring device is a system 60 configured to acquire information on the interior of the body, which is attached to the skin of the user 8 and provides monitoring data 69 for internal parts of the body including information on blood components of the user 8 to the health management server 50. This system (biological monitoring device or body monitoring terminal) 60 includes a microdialysis module 63 that inserts a microdialysis probe equipped with a semipermeable membrane into the body to collect dialysate, a Raman spectroscopy module (Raman spectroscopy) 62 that detects components in the recovered dialysate in real time, and a communication module 61 that provides (internal) monitoring data 69 on internal parts of the body including the obtained blood components via the network 9 to the health management server 50. The microdialysis module (microdialyzer) 63 is capable of recovering dialysate from inside the body, for example, a blood vessel, with hardly any burden on the user 8. By analyzing the dialysate with the Raman spectroscopy module 62, information on the interior of the living body can be gathered in real time via the network 9 using the wearable system 60. Also, by analyzing the dialysate in real time using the Raman spectroscopy module 62, it is possible to prevent the dialysate from being metabolized and producing an analysis result in which the components or concentrations have changed. The system 60 that acquires information on the interior of the body may be equipped with a non-invasive measurement module that acquires blood components in a blood vessel using light or lights from outside the skin, for example, Raman scattering (a Raman spectrum).

Figure 2:
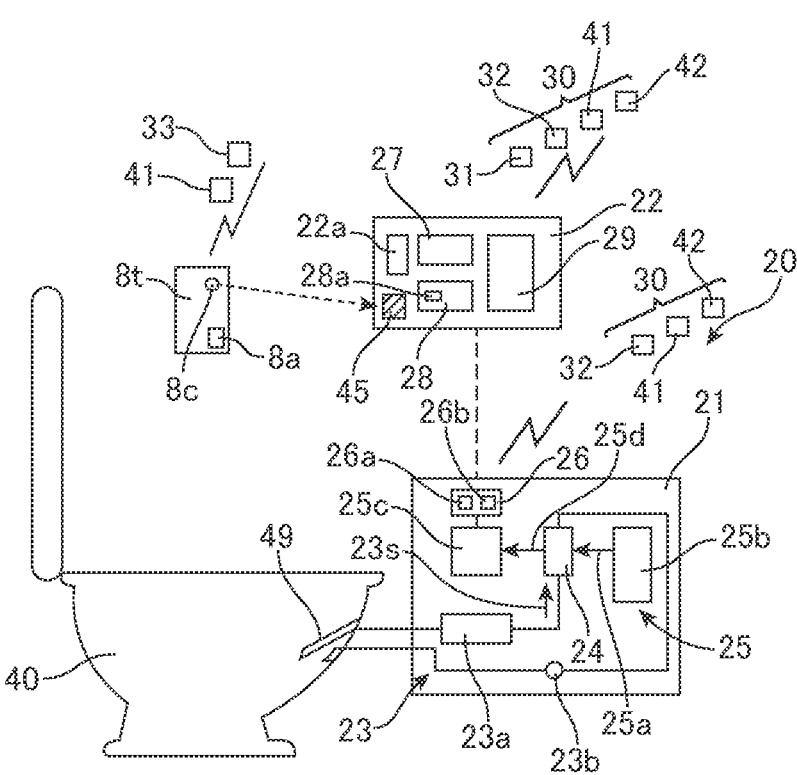
FIG. 2 is a block diagram depicting one example of a living body information acquisition system.

FIG. 2 depicts one example of the living body information acquisition system 20. The living body information acquisition system 20 includes a data acquisition module (urine testing module, urine tester, urine inspecting module, urine examination part) 21 configured to acquire body monitoring data (biological monitoring data) 32 containing information on urine components contained in a urine sample collected continuously or intermittently from at least part of the urine excreted into the toilet bowl 40, a first identification module (toilet bowl identification module, toilet bowl identifier) 45 configured so that the terminal 8t of the user 8 can acquire the toilet bowl identification information 41 for identifying the toilet bowl 40 in use by the user 8 in a contactless manner, and an output module (communication unit, communication system, communication module) 26 configured to output health monitoring information 30 of an individual including body monitoring data 32 that is associated with the user identification information 33 that identifies the user 8 who is using the toilet bowl 40 in urination units by way of the toilet bowl identification information 41. The living body information acquisition system 20 may include a second identification module (body identification module or biometric identification system) 28 configured to acquire the body identification information (biometric identification information) 31 that identifies the user 8 who is using the toilet bowl 40, and a module (communication system, communication module) 27 configured to output health monitoring information 30 of an individual including body monitoring data 32 associated with body identification information 31 in urination units.

The urine testing module (urine testing unit) 21, which is the data acquisition module, is provided corresponding to each toilet bowl 40, and as a typical configuration may be attached to the toilet bowl 40. In this body information acquisition system 20, user interface modules (user interfaces, UI modules UI units) 22 may be provided so as to one-to-one correspond to the urine testing modules 21 at positions that can be identified and only observed by the individual users of the individual toilet bowls 40, that is, the user 8 currently using each toilet bowl 40. Each UI module 22 may include a biometric identification module 28, a communication module 27, and a display 29 that provides information to the user 8. Each UI module 22 may be other any types that can be capable of identifying the user 8 in a contactless manner and providing information to the user 8.

The urine testing module 21 and the UI module 22 are associated on a one-to-one basis, may be connected by a wire or may be connected wirelessly, and may be individually connected to the network 9. The UI module 22 may be a unit that uses a smartphone terminal or a tablet terminal.

The urine testing module 21 includes a sampling module (sampler) 23 configured to continuously or intermittently collect at least part of the urine excreted into the toilet bowl 40 and discharge the urine through a translucent detecting section 24 into the toilet bowl 40, an analysis module (analyzer) 25 configured to irradiate the detecting section 24 with light 25a to acquire information on urine components (urine constituents) contained in a urine sample 23s, and a communication module (communicator) 26 configured to output body monitoring data 32 that includes information on the urine components in units of urination (urination units). The sampling module 23 includes a micropump 23a that sucks the urine sample 23s from a sampling nozzle 49 provided so as to retractably enter the toilet bowl 40 and supplies the urine sample 23*s* to the detecting section 24 which is made of a translucent member, for example, glass or transparent plastic, and forcibly circulates the urine sample 23*s* in the detecting section 24 to produce an upflow which suppresses the production of air bubbles in the detecting section 24.

The sampling module 23 includes a flow meter 23*b* that monitors the flow rate of the urine sample 23*s* flowing through the detecting section 24. The micropump 23*a* sucks the urine sample 23*s* from the sampling nozzle 49 so that a constant amount of urine is held inside the sampling nozzle 49, and causes the urine sample 23*s* to flow at a flow rate proportional to the amount of urination to the detecting section 24 to enable urine analysis to be performed. It is also possible to estimate the urination amount for one excretion by monitoring the urination time of each unit.

One example of a spectroscopic analysis module 25 that acquires information on compositions (urine components) contained in the urine sample 23*s* by irradiating the urine sample 23*s* flowing in the detecting section 24 with lights to obtain a spectrum is a Raman spectroscopy apparatus, and as particular examples it is possible to use a CARS (Coherent Anti-Stokes Raman Scattering) analyzer apparatus or SRS (Stimulated Raman Scattering) that are suited to microscopic analysis. A CARS analysis module 25 includes a laser module 25*b* that irradiates the detecting section 24 with pump light and Stokes light 25*a*, and a detection module (spectrometer) 25*c* that analyzes CARS light (a Raman spectrum) 25*d* outputted from the detecting section 24. The CARS analyzer apparatus can detect trace components in a short time and is suited to the analysis module 25 that continuously acquires information on urine components of the urine sample 23*s* that is continuously collected by the sampling module 23 and flows through the detecting section 24.

Examples of qualitative measurements for urine to be detected or examined in the analysis module 25 include glucose (GLU), protein (PRO), albumin (ALB), bilirubin (BIL), urobilinogen (URO), pH (PH), occult blood (BLD, hemoglobin, blood urine), ketone bodies (KET), nitrite (NIT), leukocytes (LEU), creatinine (CRE), albumin/creatinine ratio (A/C), and microglobulin.

The communication module 26 that outputs the body monitoring data 32 depicted in FIG. 2 includes a module 26*a* configured to output the body monitoring data 32 including progress information in which information on urine components is associated with the elapsing of the measurement time, and a module 26*b* configured to output body monitoring data 32 including progress information in which information on urine components is associated with changes over time in the urination amount. The communication module 26 may output the body monitoring data 32 together with the toilet bowl identification information 41 and/or the attribute data 42, such as a time stamp. The health management server 50, which determines the health status of the user 8 based on the body monitoring data 32, is capable of making determinations of marker components that are effective for determining the health states on various conditions such as at intermediate timing during urination, according to the average values for the entire urination of each unit, estimating the accumulated urination amount. The urination time may be determined by acquiring vibration or sound with a sensor, such as a microphone, may be determined from the amount of urine received by the sampling nozzle 49, or may be determined by the analysis module 25 detecting that water for flushing has been collected via the sampling nozzle 49.

The UI (user interface) module 22 includes a body identification module (second identification module, biometric identification information acquisition module) 28 including the camera 28*a* for acquiring the body identification information (biometric identification information) 31 through image processing, a display 29 that outputs information indicating the health status received from the health management server 50, and a communication module (output module) 27 that communicates with the health management server 50 via the network (cloud) 9. The UI module 22 may be a tablet-type terminal with a simple configuration. The UI module 22 is installed at a position where the camera 28*a* can acquire an image of the face or eyes of the user 8 who stands or sits so as to enable urination into the toilet bowl 40. Accordingly, by including the display 29 on the UI module 22, the display 29 becomes positioned so as to be easy to view for the user 8, which means information displayed on the display 29 can easily reach the user 8. For this reason, the health status may be displayed on the display 29 based on the personal health information 39 provided from the health management server 50 via the network 9. In addition, it is also possible to achieve an increased promotional effect by displaying advertisements that target the user 8 on the display 29 together with or separately to the health status. The UI module 22 may be configured solely for the purpose of providing information to the user 8 via the display 29.

The camera 28*a* may function as a motion sensor. In cases where personal information, for example, health-related information is displayed on the display 29, such information can be erased from the display 29 as soon as the user 8 moves away from the toilet bowl 40. The display 29 may be used as a touch sensor, and a fingerprint may be acquired as the biometric identification information. Also, for a toilet bowl with a flushing function, a function for checking fingerprints may be added to the switch used to perform flushing operations so that biometric identification information can be acquired.

The UI module 22 may include a user identification module 22*a* that recognizes (and/or authenticates) a terminal belonging to the user 8, as examples, the smartphone 8*t* or a wearable terminal such as a smart watch or smart glasses, via communication over an extremely short distance, for example, short-range wireless communication over several cm or less, or wireless or optical communication over a limited range, such as visible light communication whose range is limited. The user identification module 22*a* may acquire information (user identification information) 33 for identifying the user 8 who is using the toilet bowl 40 together with the body identification module 28 or in place of the body identification module 28, and the user identification information 33 may be used together with the body identification information 31 or in place of the body identification information 31. The body identification information 31 may also be used to authenticate the terminal 8*t* in the possession of the user 8.

In addition, if the terminal 8*t* of the user 8 has been authenticated and the terminal 8*t* is capable of communicating with the UI module 22 or the data acquisition module 21, the body monitoring data 32 may be provided via the terminal 8*t* to the health management server 50. That is, the communication module 27 or 26 may transmit the body monitoring data 32 to the terminal 8*t* that has been identified or authenticated as the property of the user 8 who is using the toilet bowl 40. The communication module 27 or 26 may transmit the body monitoring data 32 to the terminal 8*t* as well as the health management server 50 via the Internet 9, or may transmit the body monitoring data 32 to the terminal 8*t* via a means such as Bluetooth (registered trademark), a wireless LAN, or a mobile phone network. An application 8*a* that functions as a health management server 50 for personal use may be installed in the terminal 8*t*.

The urine testing module 21 and the UI module 22 that includes the body identification module 28 may be connected wirelessly or by using wires, and the urine testing module 21 or the UI module 22 may provide the health monitoring data 30, which includes the body identification information 31 and the body monitoring data 32, to the health management server 50 via the network 9. The communication module 27 or 26 may associate the body identification information 31 and the body monitoring data 32 in urination units and provide the information to the health management server 50 via the network 9. The urine testing module 21 and the UI module 22 may be individually connected to the network 9. If the correspondence between the urine testing module 21 and the body identification module 28 has been established in advance, the health management server 50 will be able to determine the correspondence between the body identification information 31 and the body monitoring data 32 from the time, location, and the like at which an event occurred, even if the body identification information 31 and the body monitoring data 32 are received separately via the network 9.

Figure 3:
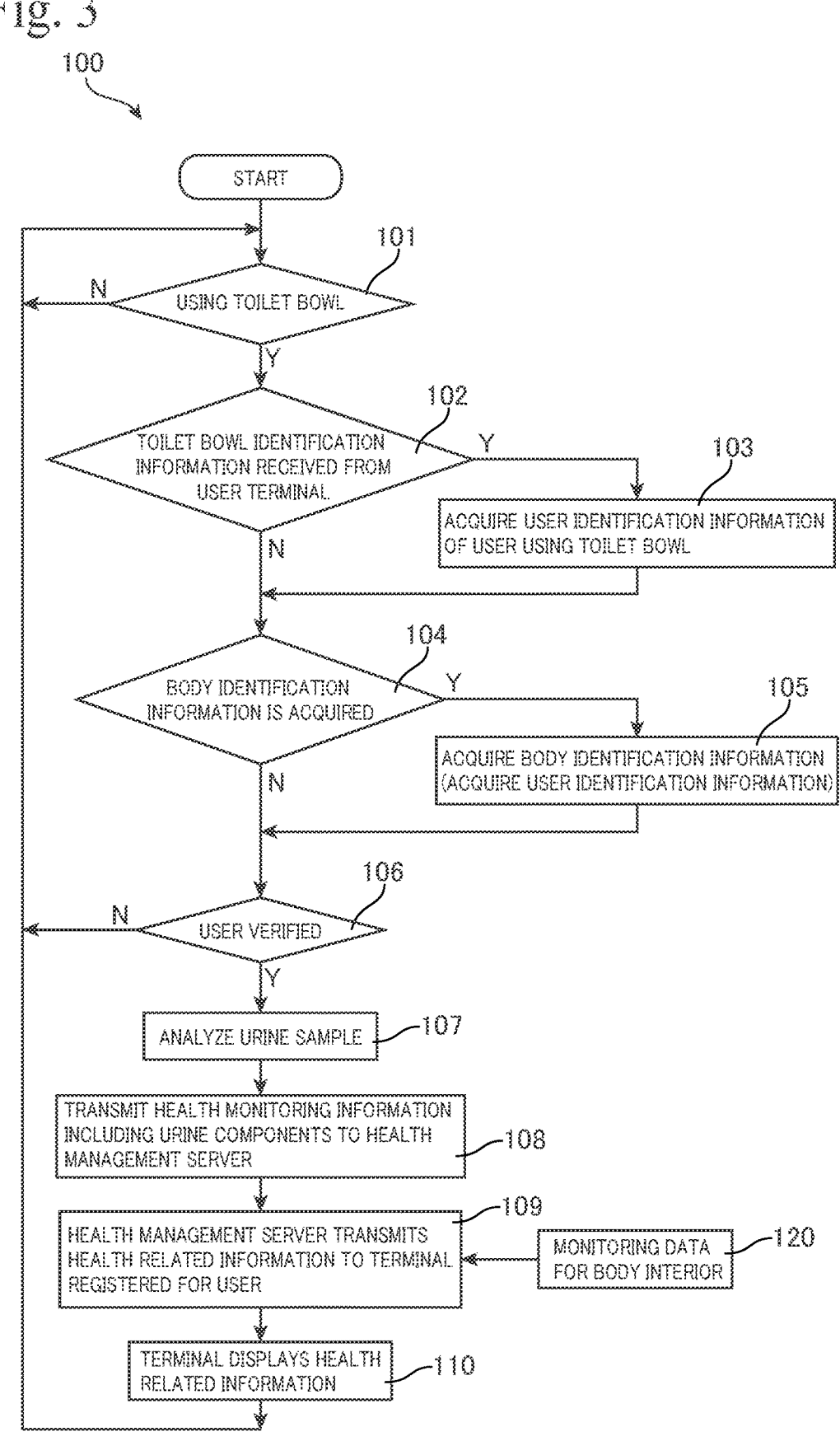
FIG. 3 is a flowchart depicting a process that feeds back information relating to health status in a health management system.

FIG. 3 depicts one example of a method 100 in which the health management system 1 supports the health of the user by feeding back information indicating the health status to the user 8 based on examinations (tests) of collected urine. In step 101, the living body information acquisition system 20 that is provided corresponding to the toilet bowl 40 determines whether use of the toilet bowl 40 has started. A start of use of the toilet bowl 40 is transmitted from the living body information acquisition system 20 to the health management server 50. The start of use of the toilet bowl 40 may be determined from transmission of the toilet bowl identification information 41 from the user terminal 8*t* or the body identification module 28 recognizing the user 8 when the user 8 is using the toilet bowl 40, or may be determined from the urine testing module 21 detecting urination. When the toilet bowl 40 is being used, the data collecting module 51 of the health management server 50 receives the toilet bowl identification information 41 from the user terminal 8*t* in step 102, and in step 103, the data collecting module 51 acquires the user identification information 33 of the user 8 who is using the toilet bowl 40 and associates the user identification information 33 with the body monitoring data 32 transmitted from the body information acquisition system 20 corresponding to that toilet bowl 40.

If the body identification information (biometric identification information) 31 can be acquired from an image acquired using the camera 28*a* of the body identification module 28 in step 104, in step 105, the user identification information 33 is acquired from the body identification information 31, and the user identification information 33 is associated with the body monitoring data 32 transmitted from the body information acquisition system 20 one-to-one corresponding to that toilet bowl 40. In step 106, if the user 8 using the toilet bowl 40 is not verified by the body identification information 31 or the like as the user 8 who has been registered in advance to use the health management server 50, analysis of the urine sample is not performed or the analysis results are discarded.

In step 107, the urine testing module 21, which is a data acquisition module, analyzes the urine sample collected from the toilet bowl 40 and acquires (generates) body monitoring data 32 including information on the urine components. The step 107 for acquiring the body monitoring data 32 may be performed before or after the steps for acquiring the toilet bowl identification information 41 and/or the body identification information 31 or may be performed in parallel. In step 108, every time urination is performed into the toilet bowl 40 (that is, for each urination unit), the communication module 26 or 27 transmits the health monitoring information 30 including the body monitoring data 32 associated with the user identification information 33 via the network to the health management server 50. When a personal health management server 50 has been installed on the terminal 8*t* of the user 8, the communication module 26 or 27 may transmit the health monitoring information 30 including the body monitoring data 32 to the terminal 8*t* using an appropriate communication method such as wireless LAN or Bluetooth (registered trademark).

In step 109, the health management server 50 analyzes the body monitoring data 32 of the user 8 identified by the user identification information 33 and provides personal information 39 relating to the health status of each user 8 via the network 9 to the terminal 8*t* that has been registered and/or authenticated for the identified user 8. The health management server 50 may feed back the personal information 39 relating to the health status to the information acquisition system 20 one-to-one corresponding to the toilet bowl 40 in use by the identified user 8 and output the personal information 39 to the display 29 of the information acquisition system 20. In addition, the health management server 50 may be provided with information 69 including blood components of the user 8 from the information acquisition system 60 connected to the network (step 120). In addition to acquiring the information 32 relating to the components excreted from the body as urine in real time using the body information acquisition system 20, the health management server 50 may acquire information 69 relating to the interior of the body including blood components in real time from the information acquisition system 60 attached to the body. The health management server 50 is capable of analyzing information relating to the body without waiting for a laboratory or the like to analyze bodily fluids such as urine and blood, and capable of transmitting (providing) information relating to the health of the user 8 to the user 8. In step 110, the terminal 8*t* of the user 8 may display the information 39 provided from the health management server 50.

Figure 4:
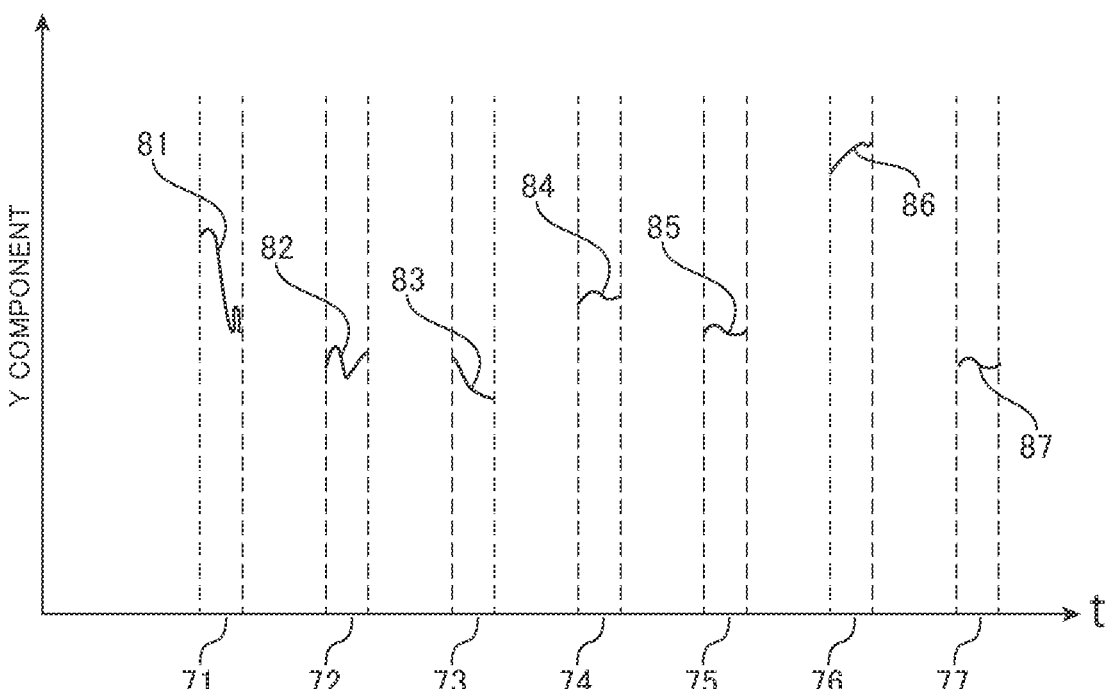
FIG. 4 depicts one example of a process of gathering body monitoring data, which includes information on urine components, during day-to-day life.

FIG. 4 depicts how the health monitoring data 30 is collected from a plurality of the living body information acquisition systems 20 by the health management server 50 in the health management system 1. When the user 8 performs urination 71 in the morning using the toilet 12 in the home 2, the living body information acquisition system 20 installed in the toilet 12 provides the health monitoring data 30 including the body monitoring data 32 containing information 81 on the urine components (for example, a Y component) via the network 9 to the health management server 50. Later, when the user 8 performs urination 72 on the way to work using the public toilet 14 in a station, the living body information acquisition system 20 installed in the public toilet 14 provides the health monitoring data 30 including the body monitoring data 32 containing information 82 on the urine components via the network 9 to the health management server 50.

When the user 8 performs urination 73 using the toilet 13 at the office 3, the living body information acquisition system 20 installed in the toilet 13 provides the health monitoring data 30 including the body monitoring data 32 containing information 83 on the urine components via the network 9 to the health management server 50. In the same way, when the user 8 performs urination 74 at lunch time using a toilet in a restaurant, the living body information acquisition system 20 installed in the restaurant toilet provides the health monitoring data 30 including the body monitoring data 32 containing information 84 on the urine components via the network 9 to the health management server 50.

In addition, when the user 8 performs urination 75 using the toilet 16 on a train 6 when going to a meeting in the afternoon, the living body information acquisition system 20 installed in the toilet 16 provides the health monitoring data 30 including the body monitoring data 32 containing information 85 on the urine components via the network 9 to the health management server 50. When the user 8 performs urination 76 using a toilet at a gym or fitness club the user 8 is using after work, the living body information acquisition system 20 installed in the gym toilet provides the health monitoring data 30 including the body monitoring data 32 containing information 86 on urine components via the network 9 to the health management server 50. Also, when the user 8 performs urination 77 at night time using the toilet 12 in the home 2, the living body information acquisition system 20 installed in the toilet 12 provides the health monitoring data 30 including the body monitoring data 32 containing the information 87 on the urine components via the network 9 to the health management server 50.

Each set of body monitoring data 32 included in each set of the health monitoring data 30 is associated with the user identification information 33 of the user 8 who and when used the toilet corresponding to the body monitoring data 32 by way of the toilet bowl identification information 41 and/or the body identification information 31 acquired at the same time. The body identification modules (biometric identification module, second identification modules) 22 that provide the body identification information 31 may be provided so as to be mainly focused on toilet bowls 40 in the form of male urinals, and the toilet bowl identification modules (first identification modules) 45 that provide the toilet bowl identification information 41 may be provided corresponding to Western-style toilets 40 installed in stalls. At the health management server 50, sets of the health monitoring data 30 sent from toilets in various locations at various timings are accumulated and analyzed for each user based on user identification information 33 that has been associated with the toilet bowl 40 at each use and each time, and it is possible to feed back personal information that is useful to the user 8 by indicating the health status and/or helping maintain the health status to the user 8 at any given time as the health-related information 39 for individuals.

One example of urine components included in the body monitoring data 32 is albumin. Urinary albumin increases over the long term when chronic kidney disease, including primary kidney disease, and factors that promote renal damage, such as hypertension and diabetes, are present. Accordingly, urinary albumin is useful in early detection of renal damage. On the other hand, urinary albumin is subject to short-term fluctuations depending on meals, water intake, posture, exercise and the like. Hence, the health status is estimated from numerical values of albumin included in urine collected (accumulated) over 24 hours and/or numerical values of albumin included in urine collected at night. The health condition may be estimated from creatinine-corrected values for spot urine samples.

The health management server 50 gathers the sets of data including urinary albumin when the user 8 urinates using toilets at various locations during the day. It is also possible to estimate the urination time and/or the amount of urination from the information included in each set of the body monitoring data 32. Accordingly, it is possible to accurately estimate the value of urinary albumin contained in urine collected over 24 hours and/or urine collected at night simply by the user 8 going about his/her normal life.

In addition, since information on urine components from the start to the end of urination (excretion) is included in each set of the body monitoring data 32 for spot urine that is excreted into a toilet at certain times, it is possible to extract urine components from an intermediate point during urination where the conditions of components are stabilized and to obtain values of urinary creatinine together with urinary albumin. Accordingly, the health status can be determined based on creatinine-corrected values of albumin and also based on urine excreted at certain times.

The health management server 50 is equipped with a urine component analysis module 54 including modules 54a to 54d that make various analysis possible, and by using the functions described above of monitoring the physical health status over a comparatively long period of time and also changes in the components in urine due to the daily activities of the user 8, it is possible to provide the user with information for maintaining health in an environment that changes in a short period of time, for example, in a hourly units, as the health information 39. As one example, when it is known from the health monitoring data 30 gathered via the cloud 9 that the intervals between urination have become longer or the concentrations of urine components have significantly increased, these suggest that hydration is inadequate, and it is possible to advise the user 8 to take measures to prevent heat stroke, economy class syndrome, and the like.

The living body information acquisition systems 20 can be easily implemented in toilets not only in Japan but all over the world. In a health management system 1 including the living body information acquisition systems 20 that have been distributed worldwide, it is possible to gather the body monitoring data 32, which includes information on urine components, via the cloud (that is, a computer network) 9 with no disturbance at all to the daily life of the user 8, which makes it possible to monitor and manage the health status of each user 8 continuously 24 hours a day, 365 days a year. The user 8 may undergo regular detailed examinations to comprehensively check his/her health status personally, and in the periods between these detailed examinations, the health management system 1 makes it possible to check excreted urine components to continuously and automatically check the user's health status individually, 24 hours a day, 365 days a year.

It is also possible to provide the user 8 with the services achieved by the health management system 1 free of charge or at a low fee that is close to free. As one example, by receiving the services of the health management system 1, it is possible to reduce the risk of the user 8 becoming affected by ill health, and for this reason, it is possible for an insurance company to reduce the risk of having to make insurance payments by providing the service to the user 8 free of charge. In addition, by providing this service free of charge, it is possible for companies involved in transportation to reduce risks, such as economy class syndrome, that can occur while transporting users as customers. This health management system 1 is also suitable as a system that efficiently provides the user 8 with information on products or services suitable for maintaining the health of the user 8 together with the health information 39 provided from the health management server 50.

Although a system that samples urine excreted into a toilet bowl has been described above as an example, it is also possible for the living body information acquisition system 20 to be a system that samples and analyzes urine excreted from a patient who is wearing a urine catheter. The health management server 50 may include a drug monitoring module 56 configured to estimate the excreted amount of a drug. As one example, many high-risk drugs need the dosage and the like to be adjusted very precisely. However, there are differences between individuals in drug metabolism, and it is burdensome to take blood samples for monitoring purposes. Many drugs are broken down in the liver and are rarely excreted in urine in the administered state or concentration. Conversely, by detecting degraded products present in urine, it is possible to monitor the usefulness of a drug. Many patients receiving such drugs have a urinary catheter inserted, and by monitoring urine components excreted into the urinary catheter, it is possible to monitor the patient's condition, including the effect of medication, continuously for 24 hours. In addition, it is thought easy to perform monitoring when antibiotics are being administered since most of them are excreted in an undegraded state into the urine.

A combination of the living body information acquisition systems 20 that can acquire monitoring data 32, including components in urine, in real time and the systems 60 that can acquire monitoring data 69 for the interior of the body, including blood components, in real time is effective for pharmacokinetic/pharmacodynamic (PK/PD) modeling, which is an important component in the development process for new drugs and the like. PK/PD modelling is one of the mathematical methods for predicting the effect and effectiveness of administrating a drug over time. A pharmacokinetic model expresses the body's response to a drug in terms of absorption, distribution, metabolism, and excretion, and a pharmacodynamic model expresses the effects of a drug on the body by linking drug concentration to efficacy (or safety). A PK/PD model (or "personal PK/PD model") that has been clearly characterized for an individual can be an important tool in guiding the design of tailor-made medicines. The drug monitoring module 56 of the health management server 50 generates a PK/PD model that is suited to the user 8 by acquiring blood components and urine components in real time for a drug that has been prescribed to the user 8 and, in addition to verification, is capable of monitoring changes over time continuously in real time or in an environment close to real time.

Examples of substances to be measured in order to verify pharmacokinetics through the performance of therapeutic drug monitoring include drugs (mainly antibiotics) and high-risk drugs that are excreted in urine. Examples of high-risk drugs may include quinidine, vancomycin, acetaminophen, carbamazepine, mycophenolate mofetil, salicylic acid, phenytoin, cyclosporine, valproic acid, primidone, procainamide, phenobarbital, procainamide metabolites, and lidocaine.

The substances subjected to testing or detecting by the living body information acquisition system (biological information acquisition system) 20 are not limited to the components given as examples in the above description and may be various components (constituents) contained in urine, for example, cancer markers and target substances in doping tests. The living body information acquisition system 20 disclosed above can be used in combination with another system, for example, a system for storing urine samples for a laboratory, and the present invention is not limited to the example system described above.

Note that the systems, apparatuses, images, example cases, and information such as numerical values disclosed above are mere examples, and the present invention is not limited to the description and illustrations given here. Although specific embodiments of the present invention have been described above with reference to the attached drawings, a variety of other embodiments and modifications should be obvious to those of skill in the art without departing from the scope and spirit of the invention. Such other embodiments and modifications are also covered by the range of the patent claims given below in which the scope of the present invention is defined.

The invention claimed is:

1. A living body information acquisition system comprising: a first identification supplier configured to supply toilet bowl identification information that identifies a toilet bowl, which is used publicly by unspecified users, in use by a user to a terminal of the user in a contactless manner; a detector configured for detecting urination by the unspecified users a urine tester including the detector and configured to automatically acquire body monitoring data including information on urine components contained in urine samples collected continuously or intermittently from at least part of urine excreted into a toilet bowl when the detector detects a urination of the unspecified users; wherein the urine tester includes a module that irradiates a detecting section with laser energy to acquire Raman spectra to acquire information on the urine components contained in the urine samples; a health management server that is configured to analyze the body monitoring data; an interface module that receives the body monitoring data from the data acquisition module and automatically transfers the body monitoring data with the toilet bowl identification information when the toilet bowl is used by the unspecified users to the health management server; and the health management server includes a database that accumulates the body monitoring data, with the respective toilet bowl identification information, received from the interface module and converts the body monitoring data to health monitoring information; wherein the health management server is further configured to automatically output the health monitoring information of the user to the terminal of the user, by way of the toilet bowl identification information sent from the terminal of the user.

2. The living body information acquisition system according to claim 1, wherein the first identification supplier includes a two-dimensional code.

3. The living body information acquisition system according to claim 1, further comprising an identification module configured to acquire body identification information associated with user identification information that identifies the user when using the toilet bowl.

4. The living body information acquisition system according to claim 3, wherein the identification module includes a module configured to acquire the body identification information by image processing.

5. The living body information acquisition system according to The living body information acquisition system according to claim 1, wherein the urine tester includes: a sampling module configured to continuously or intermittently collect at least part of excreted urine and discharge the urine through a translucent detecting section; and an analysis module configured to irradiate the detecting section with light to acquire information on the urine components contained in the urine samples.

6. The living body information acquisition system according to claim 1, wherein the urine tester includes a module configured to output the body monitoring data including progress information in which information on the urine components is associated with passage of measurement time.

7. The living body information acquisition system according to claim 1, wherein the urine tester includes a module configured to output the body monitoring data including progress information in which information on the urine components is associated with passage of time of urination volume.

8. The living body information acquisition system according to claim 3, wherein the interface module is configured to provide the body monitoring data associated with user identification information in urination units via a network to the health management server.

9. The living body information acquisition system according to claim 8, further comprising a display that outputs information from the health management server.

10. A method of supporting health of individuals via information acquisition systems corresponding to toilet bowls respectively, wherein the toilet bowls are used publicly by unspecified users, and each of the information acquisition systems corresponding to each of the toilet bowls includes a data acquisition module configured to automatically detect urine components contained in urine samples collected continuously or intermittently from at least part of urine excreted into a corresponding toilet bowl; a first identification supplier configured so that a terminal of the user acquires toilet bowl identification information that identifies the corresponding toilet bowl in use by the user, in a contactless manner; and an output module, and the method comprises: detecting urination by the unspecified users; using the data acquisition module to irradiate the urine samples with lasers to acquire Raman spectra, the data acquisition module acquiring body monitoring data including information on the urine components automatically when urination is detected by the unspecified users; identifying the user when using the corresponding toilet bowl by way of the toilet bowl identification information obtained from the terminal of the user before, after, or in parallel with acquisition of the body monitoring data with the toilet bowl identification information; and the output module automatically outputting personal health monitoring information including the body monitoring data to the terminal of the user by way of the toilet bowl identification information sent from the terminal of the user.

11. The method according to claim 10, further comprising a health management server configured to convert the body monitoring data associated with the user identification information to health monitoring information relating to a health status of the user and providing the health monitoring information via a network to a display of a body information acquisition system corresponding to a toilet bowl in use by the identified user or to a terminal of the identified user.

12. The method according to claim 11, further comprising a system that acquires information on a body interior supplying monitoring data on the body interior, which includes information on blood components of the user, via a network to the health management server.

13. A living body information acquisition system comprising: a first identification supplier configured to supply toilet bowl identification information that identifies a toilet bowl, which is used publicly by unspecified users, in use by a user to a terminal of the user in a contactless manner; a detector configured for detecting urination by the unspecified users; a data acquisition module including the detector and configured to automatically acquire body monitoring data including information on urine components contained in urine samples collected continuously or intermittently from at least part of urine excreted into a toilet bowl when urination by the unspecified users is detected by the detector; wherein the data acquisition module includes an analysis module configured to irradiate a detecting section to acquire information on the urine components contained in the urine samples, and the analysis module includes a module configured to irradiate the urine samples with lasers to acquire Raman spectra; and an interface module configured to receive the body monitoring data from the data acquisition module and to automatically transfer the body monitoring data with the toilet bowl identification information when the toilet bowl is used by the unspecified users to a health management server via a network; wherein the health management server is further configured to automatically output the health monitoring information of the user to the terminal of the user, by way of the toilet bowl identification information sent from the terminal of the user.

14. The living body information acquisition system according to claim 13, further comprising the health management server, wherein the health management server is configured to analyze the body monitoring data.

* * * * *